(12) United States Patent
Keitel

(10) Patent No.: US 10,272,210 B2
(45) Date of Patent: Apr. 30, 2019

(54) INJECTION DEVICE AND METHOD FOR MAKING THE SAME

(71) Applicant: Haselmeier AG, St. Gallen (CH)

(72) Inventor: Joachim Keitel, Esslingen (DE)

(73) Assignee: Haselmeier AG, St. Gallen (CH)

( * ) Notice: Subject to any disclaimer, the term of this patent is extended or adjusted under 35 U.S.C. 154(b) by 124 days.

(21) Appl. No.: 14/153,682

(22) Filed: Jan. 13, 2014

(65) Prior Publication Data

US 2014/0128808 A1 May 8, 2014

Related U.S. Application Data

(63) Continuation of application No. PCT/EP2012/002964, filed on Jul. 13, 2012.

(30) Foreign Application Priority Data

Jul. 13, 2011 (DE) .................. 10 2011 107 199

(51) Int. Cl.
*A61M 5/46* (2006.01)
*A61M 5/32* (2006.01)

(52) U.S. Cl.
CPC ............ *A61M 5/3287* (2013.01); *A61M 5/46* (2013.01); *Y10T 29/494* (2015.01)

(58) Field of Classification Search
CPC ...... A61M 5/31583–5/31586; A61M 5/31575; A61M 5/31571; A61M 5/31565;
(Continued)

(56) References Cited

U.S. PATENT DOCUMENTS 4,865,591 A * 9/1989 Sams ................ A61M 5/31553
604/186
5,042,977 A * 8/1991 Bechtold ................. A61M 5/20
604/134
(Continued)

FOREIGN PATENT DOCUMENTS

WO WO 2006/063015 A2 6/2006
WO WO 2008/048750 A2 4/2008
(Continued)

OTHER PUBLICATIONS

International Search Report dated Oct. 10, 2012 of international application PCT/EP2012/002964 on which this application is based.

*Primary Examiner* — Jenna Zhang
(74) *Attorney, Agent, or Firm* — Walter Ottesen, P.A.

(57) ABSTRACT

An injection device has a housing which includes a first housing part and a second housing part. The injection device has a receptacle for an injection needle. The receptacle is connected to a drive unit which moves the receptacle between proximal and distal end positions relative to the second housing part. The first housing part has a set piece for placing on the skin before triggering an injection. The first housing part is permanently fastened with respect to the second housing part. In a method for making the injection device, the first housing part is positioned on the second housing part so that the receptacle has a specified position relative to the set piece in the proximal end position thereof, and that the first housing part is permanently fastened in this position opposite the second housing part. A defined insertion depth can thus be ensured.

20 Claims, 8 Drawing Sheets

(58) Field of Classification Search
CPC .......... A61M 5/31528; A61M 5/31533; A61M 5/31525; A61M 5/3159; A61M 5/31511; A61M 5/31515; A61M 5/46; A61M 5/50; A61M 5/502; A61M 5/2033; A61M 5/3287; A61M 5/5013; A61M 5/504; A61M 5/5066; A61M 5/508
See application file for complete search history.

(56) References Cited

U.S. PATENT DOCUMENTS

| | | | | |
|---|---|---|---|---|
| 5,092,842 | A * | 3/1992 | Bechtold | A61M 5/20 604/135 |
| 5,114,406 | A * | 5/1992 | Gabriel | A61M 5/2033 604/134 |
| 5,478,316 | A * | 12/1995 | Bitdinger | A61M 5/2033 604/134 |
| 5,514,097 | A * | 5/1996 | Knauer | A61M 5/20 604/136 |
| 6,004,297 | A * | 12/1999 | Steenfeldt-Jensen | A61M 5/31551 604/207 |
| 6,221,046 | B1 * | 4/2001 | Burroughs | A61M 5/31551 604/153 |
| 6,241,709 | B1 | 6/2001 | Bechtold et al. | |
| 6,391,003 | B1 * | 5/2002 | Lesch, Jr. | A61M 5/30 604/110 |
| 6,482,176 | B1 | 11/2002 | Wich | |
| 7,918,832 | B2 * | 4/2011 | Veasey | A61M 5/31585 604/207 |
| 9,364,610 | B2 * | 6/2016 | KraMer | A61M 5/20 |
| 9,364,611 | B2 * | 6/2016 | KraMer | A61M 5/20 |
| 2002/0045866 | A1 * | 4/2002 | Sadowski | A61M 5/20 604/208 |
| 2002/0165500 | A1 * | 11/2002 | Bechtold | A61M 5/2033 604/209 |
| 2003/0171717 | A1 * | 9/2003 | Farrugia | A61M 5/2033 604/131 |
| 2004/0210199 | A1 * | 10/2004 | Atterbury | A61M 5/31535 604/224 |
| 2005/0165363 | A1 * | 7/2005 | Judson | A61M 5/24 604/209 |
| 2006/0258988 | A1 * | 11/2006 | Keitel | A61M 5/31551 604/181 |
| 2010/0049125 | A1 * | 2/2010 | James | A61M 5/2033 604/110 |
| 2012/0095413 | A1 * | 4/2012 | Nzike | F16H 31/001 604/211 |
| 2012/0265151 | A1 * | 10/2012 | Nzike | A61M 5/31543 604/211 |
| 2013/0226091 | A1 * | 8/2013 | Nzike | A61M 5/31525 604/131 |
| 2013/0317431 | A1 * | 11/2013 | KraMer | A61M 5/20 604/131 |

FOREIGN PATENT DOCUMENTS

| | | |
|---|---|---|
| WO | WO 2009/155277 A1 | 12/2009 |
| WO | 2010/108116 A1 | 9/2010 |

* cited by examiner

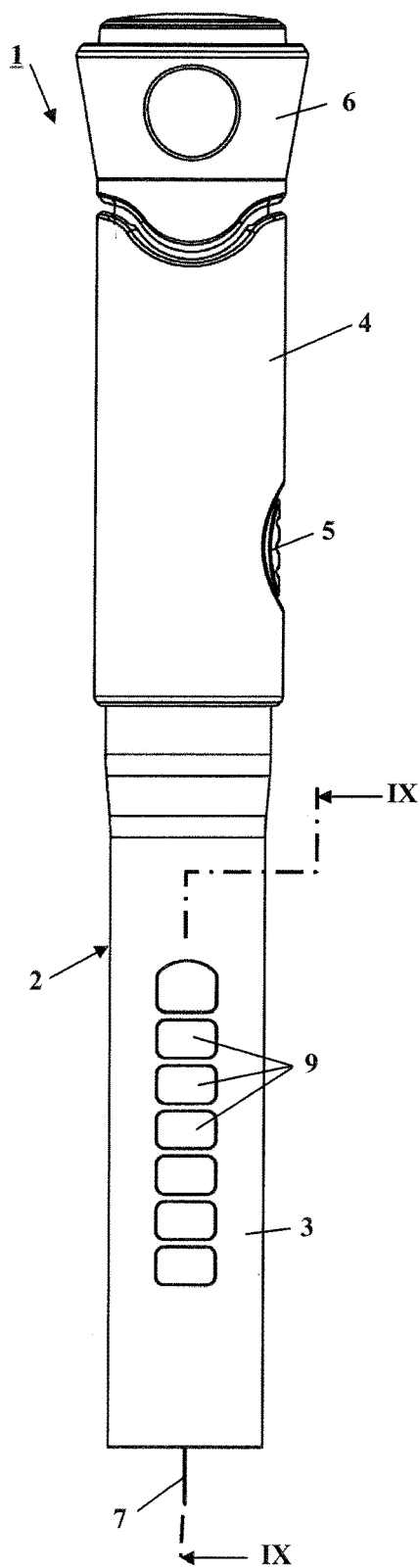
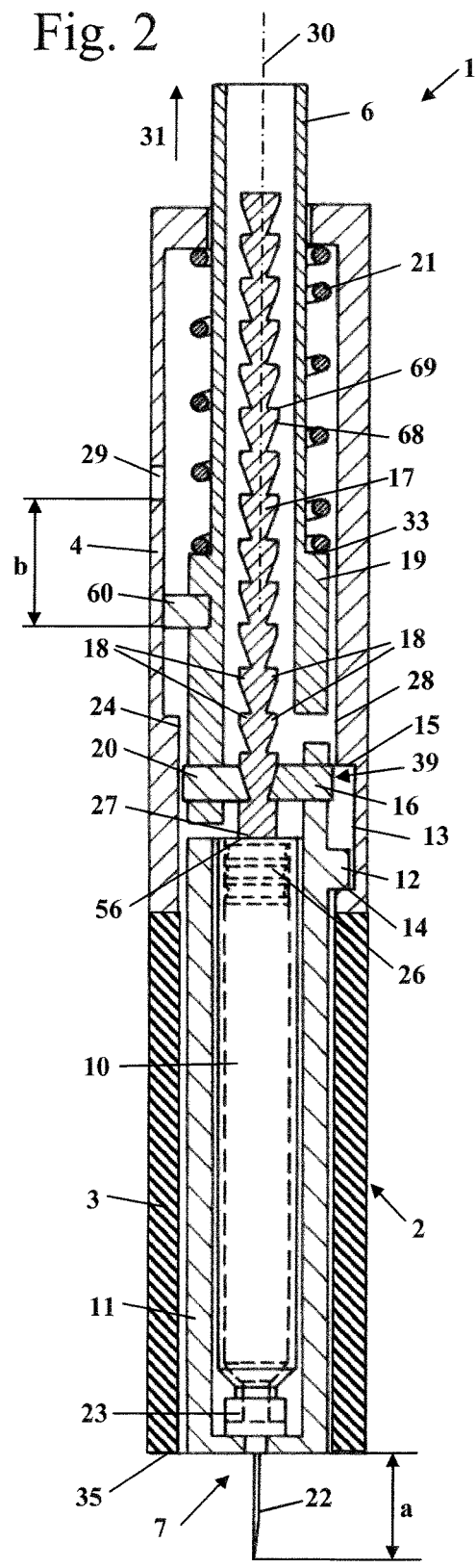

Fig. 3
Fig. 4
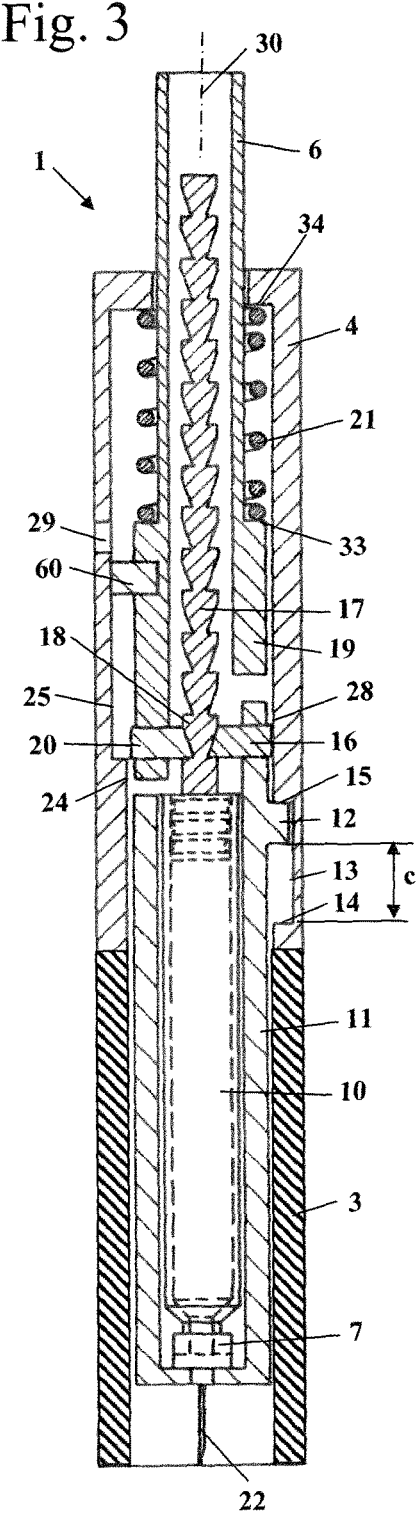
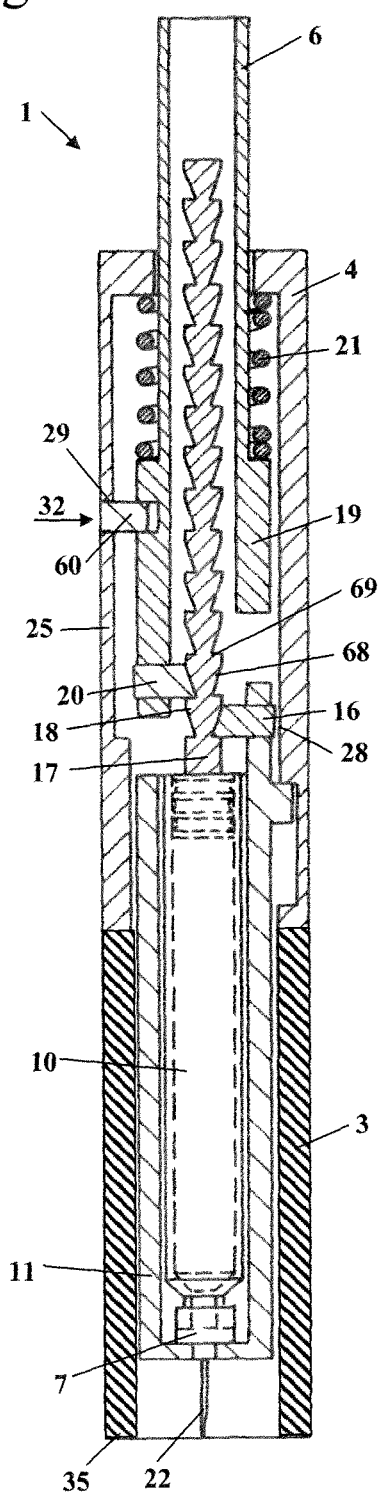

Fig. 5
Fig. 6
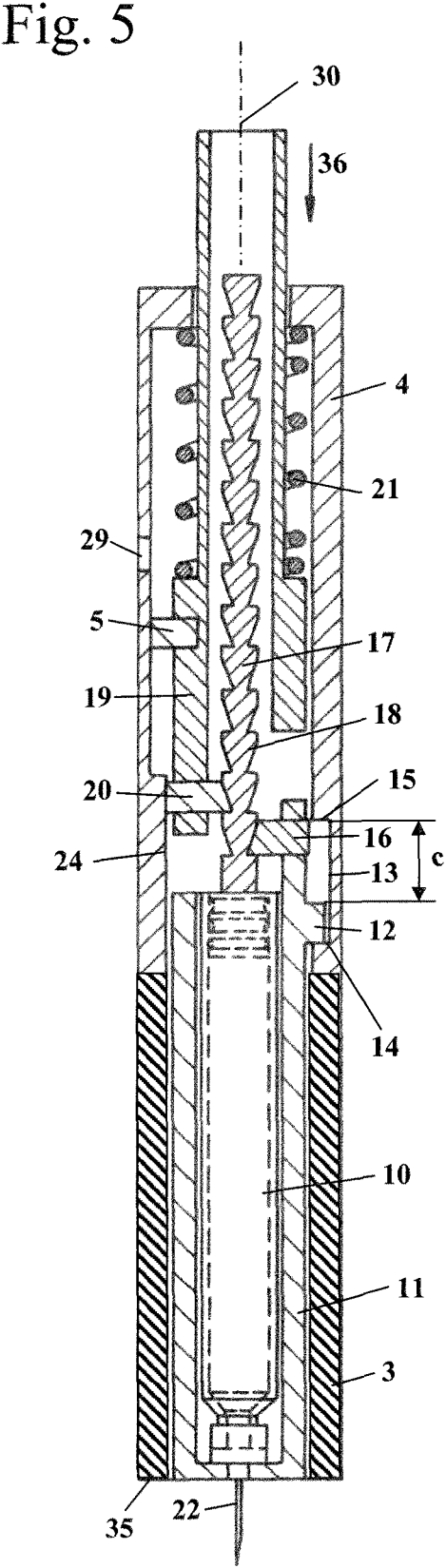
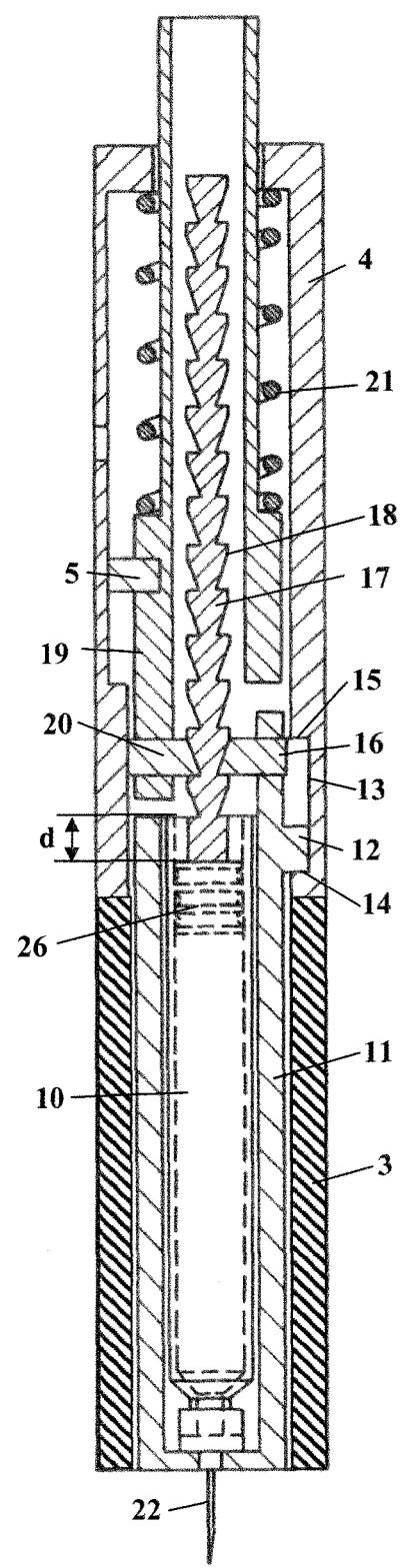

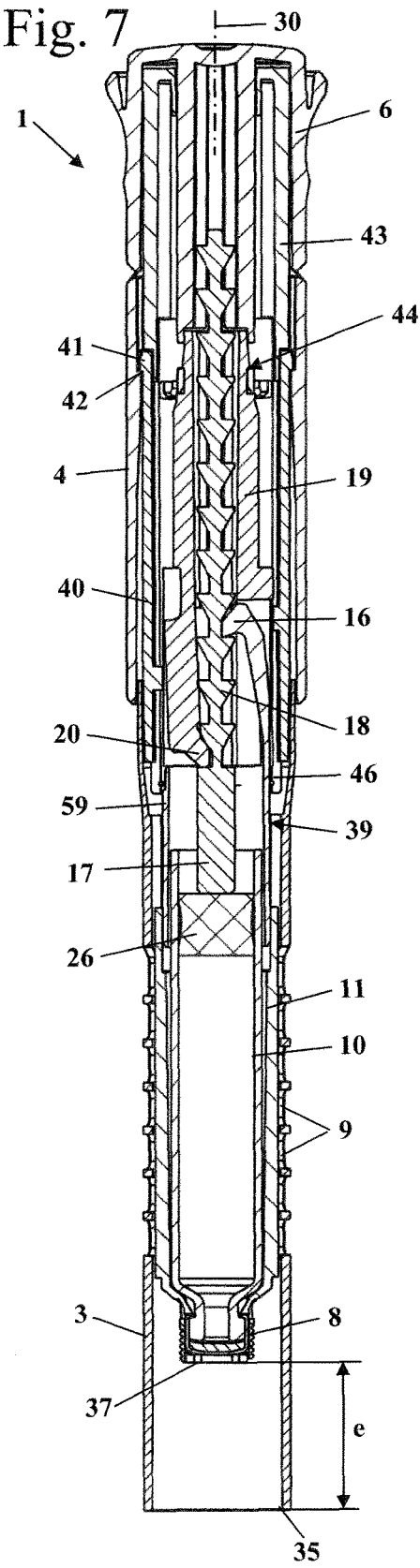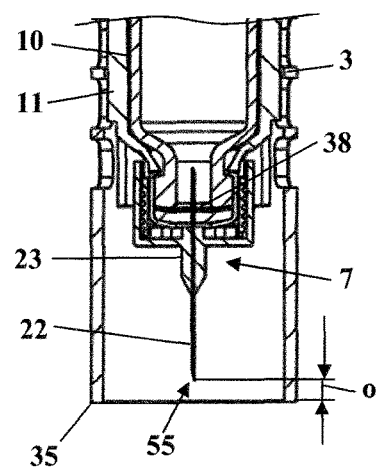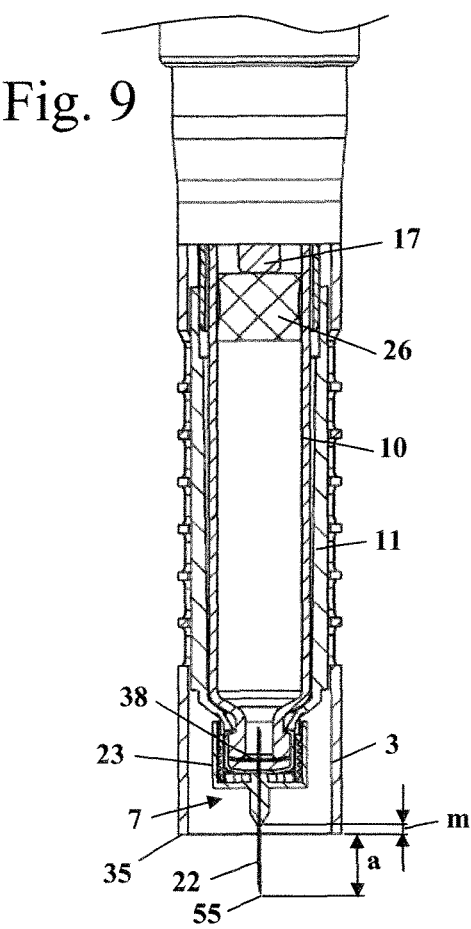

Fig. 10
Fig. 11
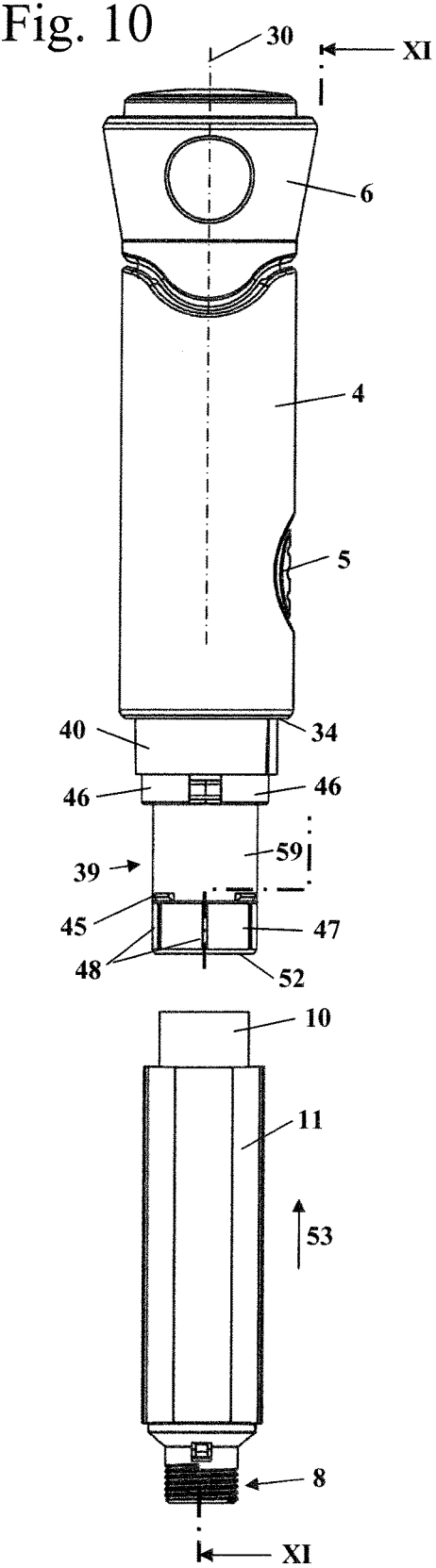
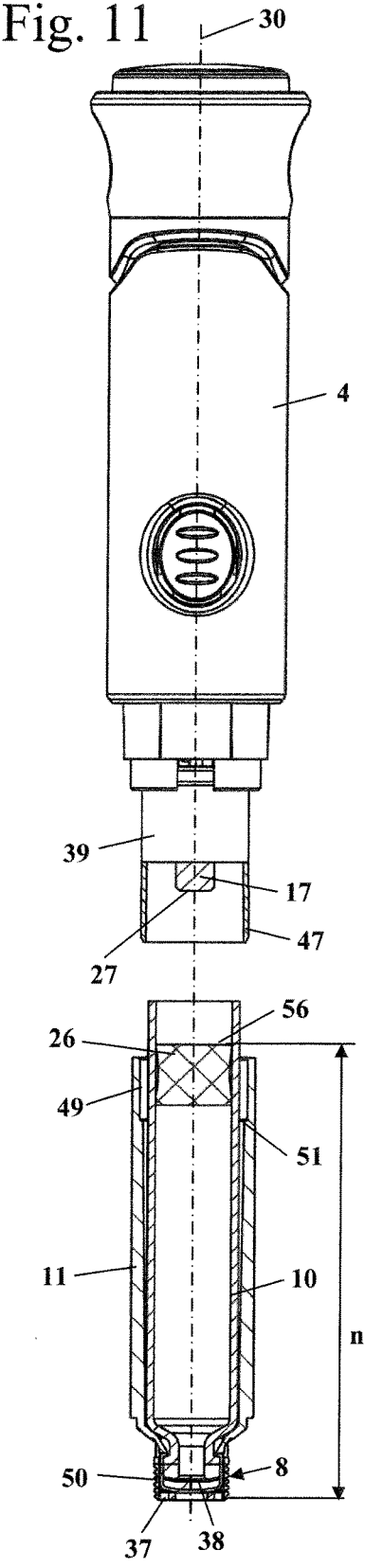

Fig. 12
Fig. 13
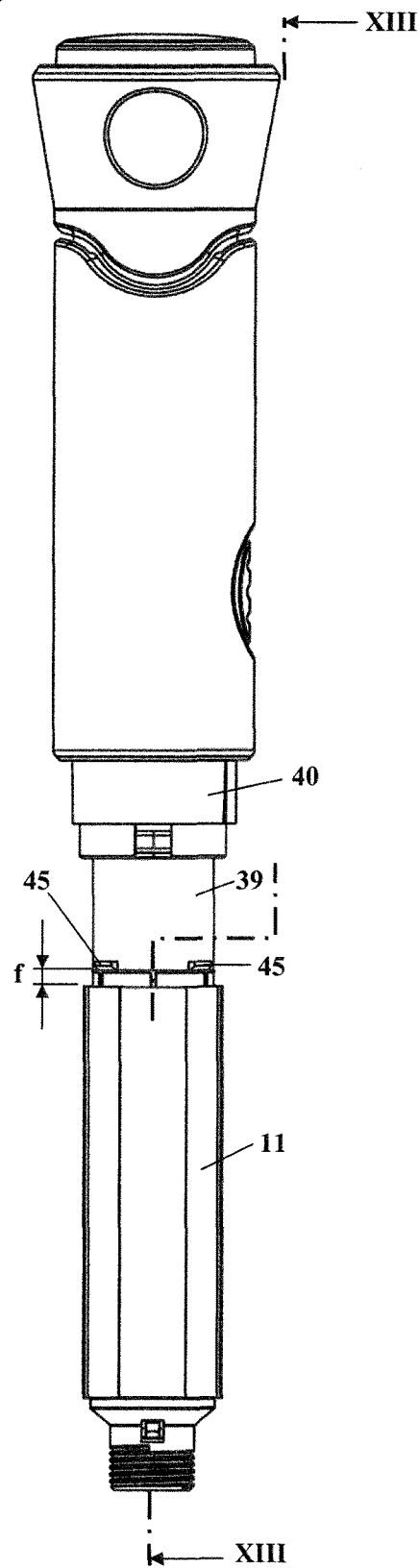
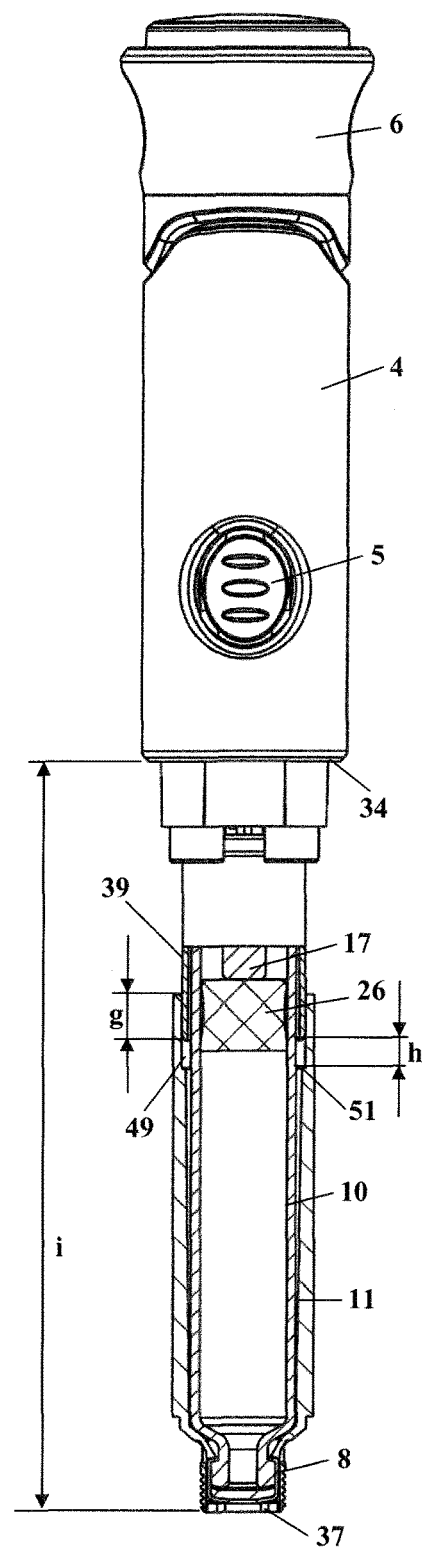

Fig. 14
Fig. 15
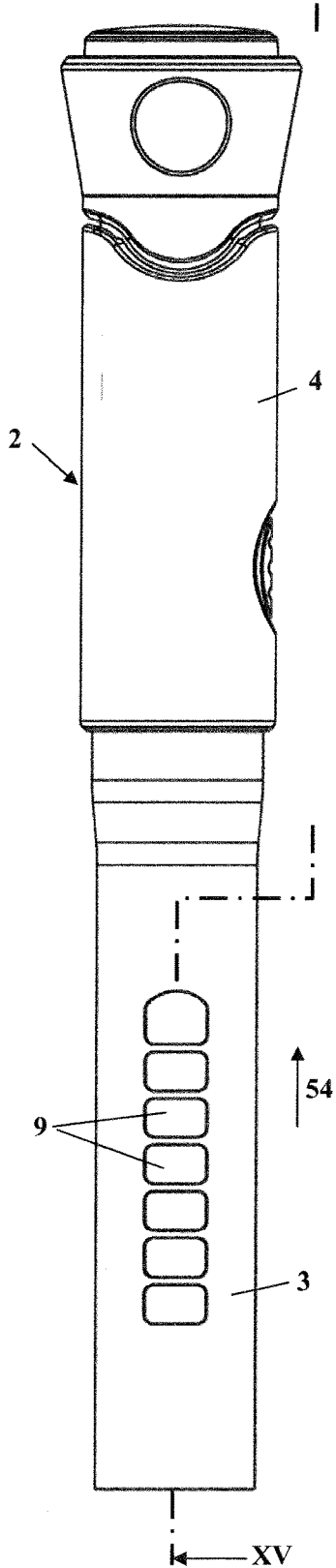
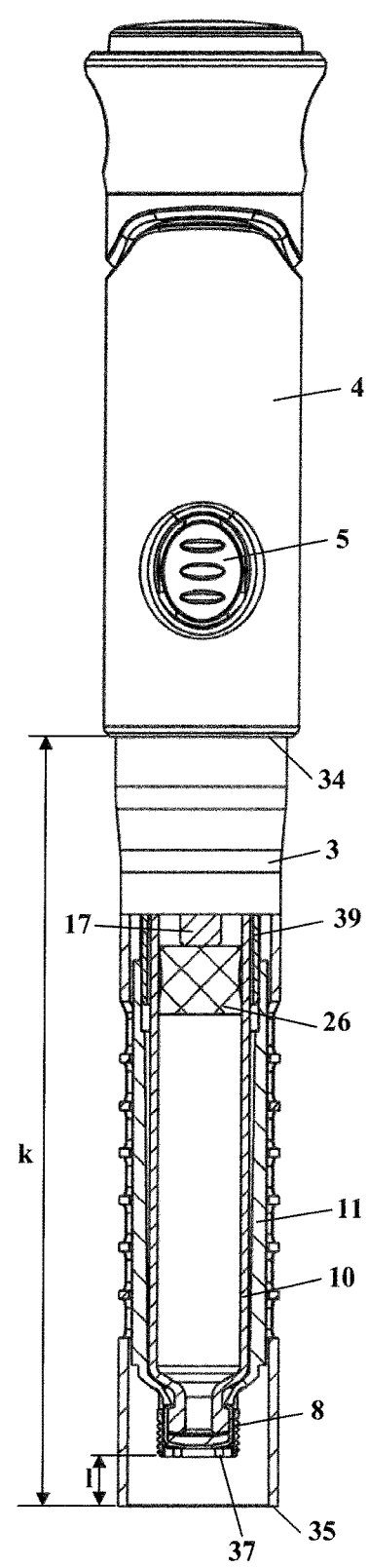

INJECTION DEVICE AND METHOD FOR MAKING THE SAME

CROSS REFERENCE TO RELATED APPLICATIONS

This application is a continuation application of international patent application PCT/EP2012/002964, filed Jul. 13, 2012, designating the United States and claiming priority from German application 10 2011 107 199.0, filed Jul. 13, 2011, and the entire content of both applications is incorporated herein by reference.

BACKGROUND OF THE INVENTION

U.S. Pat. No. 6,241,709 discloses an injection device, in which a holder, which carries an injection needle and in which a carpule containing injection fluid is arranged, is moved relative to the housing. By retraction of the holder, the injection needle is concealed in the housing before the injection operation. This reduces the user's anxiety about the needle.

In order to make the injection device, it is known from U.S. Pat. No. 6,241,709 to arrange the holder for the carpule containing injection fluid on the driving device in such a manner that the plunger, which serves to inject injection fluid from the container, bears against the stopper of the carpule before the first injection. A micro-grid structure is provided in U.S. Pat. No. 6,241,709 in order to fix the holder.

The production process causes the position of the stopper in the carpule to be subject to comparatively high tolerances. A different position of the injection needle in the housing therefore arises depending on the position of the stopper. Since the distance which the container covers in relation to the housing is structurally predetermined, the insertion depth changes in dependence on the position of the injection needle. In order to control the insertion depth, a sleeve with which the insertion depth can be changed manually by the operator is known from U.S. Pat. No. 6,241,709.

For certain applications, it is advantageous to carry out the injection with a precisely defined insertion depth. This is expedient in particular if the injection is carried out with a very short injection needle. In the case of very short injection needles, it firstly has to be ensured that a sufficient insertion depth is reached so that the injection fluid is securely injected. Secondly, it has to be ensured that the needle holder does not emerge too far out of the housing.

SUMMARY OF THE INVENTION

It is an object of the invention to provide a method for making an injection device, with which a desired insertion depth can be ensured. It is a further object of the invention to provide an injection device which has a defined insertion depth.

The injection device has a multi-part housing which includes at least one first and one second housing part. The two housing parts are positioned relative to one another during the making of the injection device. The positioning takes place in such a manner that the receptacle, in the proximal end position thereof, has a predetermined position relative to the support. In this position, the first housing part is then fixed nonreleasably in relation to the second housing part. The first housing part is in particular fixed directly to the second housing part. However, the first housing part can also be fixed to a component which is connected fixedly to the second housing part. Nonreleasable fixing is understood as meaning fixing which cannot be released by the user without damaging the injection device. As a result, the insertion depth once set during production by positioning the two housing parts with respect to each other cannot be changed by the operator. Owing to the positioning of the two housing parts with respect to each other, manufacturing tolerances between the individual parts of the injection device can be compensated for, and the insertion depth can be determined within the framework of the accuracy of positioning the two housing parts with respect to each other.

The present invention is provided for injection devices which are not refillable. Injection devices of this type have a container containing injection fluid, namely what is referred to as a carpule or cartridge. The injection fluid is sufficient for a plurality of injections. After the final injection, the injection device is disposed of.

In order to expel the injection fluid, a movable stopper is arranged in the container. The driving device advantageously has a plunger which acts on the stopper. Injection fluid can be squeezed out of the container via the plunger. So that, even during the first injection, a defined quantity of injection fluid is injected, provision is made for the container to be positioned relative to the plunger in such a manner that a defined position of the stopper relative to the plunger is produced, and for the container to be fixed in this position. This makes it possible to avoid the user first of all having to discard a small quantity of injection fluid in order to ensure that the plunger bears against the stopper. The container can be positioned in such a manner that the plunger bears against the stopper, but it may also be advantageous if a defined spacing is set between the plunger and the stopper. This defined spacing has to be taken into consideration structurally for the metering distance for the first injection.

The positioning of the container relative to the plunger advantageously takes place before the positioning of the first housing part relative to the second housing part. The tolerances in the position of the stopper can therefore be compensated for via the positioning of the first housing part on the second housing part. As a result, firstly, a very precise insertion depth can be achieved and, secondly, the use of containers containing injection fluid, in which containers the position of the stopper is less precisely defined, is possible. This simplifies the production.

The injection device advantageously has a coupling element which interacts with the plunger. Advantageously, after the positioning relative to the plunger, the container is fixed in relation to the coupling element. As a result, the container can be positioned in relation to the plunger in a simple manner. In particular, the container is arranged in a holder which carries the receptacle, and the holder, with the container arranged therein, is fixed to the coupling element. The receptacle is therefore positioned relative to the driving device via the holder and the coupling element.

Simple production results if the first housing part is adhesively bonded to the second housing part. Use is advantageously made of an adhesive which cures by means of radiation, in particular by means of UV radiation. However, provision can also be made for the first housing part to be pressed to the second housing part. Particularly advantageously, the pressing is undertaken by hot pressing. Provision can also be made for the first housing part to be welded to the second housing part. The welding is advantageously undertaken via laser welding or ultrasonic welding.

An injection device which ensures a defined insertion depth has a housing with a first and a second housing part, wherein the first housing part is fixed nonreleasably in relation to the second housing part. The first housing part is fixed in particular directly to the second housing part. The multi-part configuration of the housing permits precise positioning of the housing parts relative to each other, and therefore the insertion depth can be set precisely. As a result of the fact that the two housing parts are connected fixedly to each other, a later change in the insertion depth by the operator is precluded.

In order to ensure that, even during the first injection, a preset quantity of injection fluid is injected, provision is made for the plunger to bear against the movable stopper of the container. However, provision can also be made for the plunger to have a spacing from the stopper before the first injection, and for the driving device to be configured in such a manner that, during the first injection, the plunger covers a distance which is greater by the spacing between plunger and stopper than the distance required for squeezing out the set quantity of injection fluid. This can take place by appropriately increasing the regulating distance for the first injection.

The container is advantageously connected to a coupling element which interacts with the plunger. The coupling element fixes the plunger relative to the container or releases the plunger in relation to the container, depending on the operating state. Different operating states here include the first phase of tensioning the injection device, in which the injection needle is retracted into the housing, the second phase of tensioning the injection device, in which the driving device is adjusted in relation to the plunger by the distance which corresponds to the quantity of fluid to be injected, the insertion of the needle and the injection of the injection fluid.

The container is advantageously held in a holder which has the receptacle for the injection needle. As a result, the container itself can be of simple construction. The holder is advantageously made of a transparent material. With an appropriate configuration of the housing, the user can thereby see through the holder how much injection fluid is still present in the container. As a result of the transparent design of the holder, the holder can be connected to the coupling element via an adhesive connection which is cured by means of radiation, in particular by means of UV radiation. A fixed, nonreleasable connection of holder and coupling element can thereby be achieved in a simple manner. The holder and the coupling element are, in particular, made of plastic.

Provision is made for the injection device to have a tension spring which, during the injection operation, brings about both a movement of the container relative to the housing and a movement of the plunger relative to the container. Thus, with one tension spring, both the insertion of the injection needle and the injection of the injection fluid can be brought about. This results in a simple construction of the injection device. The driving device is advantageously connected to the container and to the plunger via a coupling device. The coupling device is, in particular, controlled in dependence on the position of driving device, container and plunger relative to the housing. Accordingly, a distance-dependent control of the coupling device is provided. The coupling device can be realized in particular in the form of a cam-controlled pawl coupling. The coupling device advantageously controls a first connection between the container and the plunger and a second connection between the plunger and the driving device. Through an appropriate activation of the two connections, the coupling device can also connect the container to the driving device.

BRIEF DESCRIPTION OF THE DRAWINGS

The invention will now be described with reference to the drawings wherein:

FIG. 1 is a side view of an injection device;

FIG. 2 is a schematic sectional view through the injection device in the inoperative state;

FIG. 3 shows a sectional view corresponding to FIG. 2 after retraction of the needle;

FIG. 4 shows a sectional view corresponding to FIG. 2 after complete tensioning of the tension spring;

FIG. 5 shows a sectional view corresponding to FIG. 2 after insertion of the injection needle;

FIG. 6 shows a sectional view corresponding to FIG. 2 after injection of the injection fluid;

FIG. 7 shows a section through the injection device of FIG. 1 after retraction of the container and without an injection needle;

FIG. 8 shows a partial view of the region of the receptacle of the injection device of FIG. 7 with an injection needle arranged thereon;

FIG. 9 shows a section along the line IX-IX in FIG. 1;

FIG. 10 shows the injection device of FIG. 1 before mounting of the holder;

FIG. 11 shows a section along line XI-XI in FIG. 10;

FIG. 12 shows a side view of the injection device of FIG. 10 after insertion of the holder;

FIG. 13 shows a section along the line XIII-XIII in FIG. 12;

FIG. 14 shows a side view of the injection device of FIG. 10 after installation of the first housing part;

FIG. 15 shows a section along the line XV-XV in FIG. 14; and,

Figure 16:
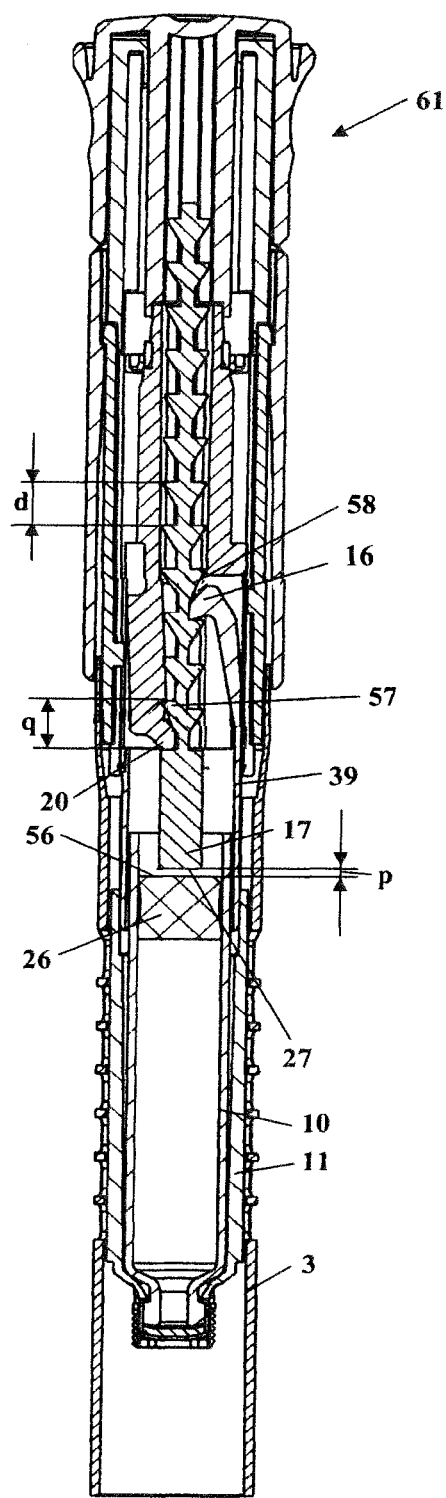
FIG. 16 shows a longitudinal section through an exemplary embodiment of an injection device.

DESCRIPTION OF THE PREFERRED
EMBODIMENTS OF THE INVENTION

FIG. 1 shows an injection device 1. The injection device 1 is approximately in the form of a large fountain pen or ballpoint pen and serves to inject an injection fluid. The injection device shown in FIG. 1 is not refillable. With the injection device 1, a predetermined number of injections can be carried out. The quantity of fluid to be injected per injection is structurally predetermined here. However, injection devices are also known, for example from U.S. Pat. No. 6,241,709, in which the quantity of fluid to be injected can be set by the operator. The present invention is also provided for injection devices in which the quantity to be injected can be set.

The injection device 1 has a housing 2 which is configured in two parts. The housing 2 has a first, proximal housing part 3 and a second, distal housing part 4. "Proximal" here denotes the end which faces the insertion point during an injection and "distal" denotes the end which faces away from the insertion point. In the unactuated position of the injection device 1 that is shown in FIG. 1, an injection needle 7 protrudes from the first housing part 3. The first housing part 3 has a plurality of viewing windows 9 which are configured as openings in the housing part 3, which is made from opaque plastic. The container containing injection fluid is visible through the viewing windows 9.

For operating purposes, the distal end of the injection device 1 has a tensioning element 6 which can be pulled out of the housing 2 by the operator in order to tension the injection device 1, and a triggering element 5, which is configured as an operating button and is arranged on the second housing part 4. In order to trigger an injection, the operator places the tensioned injection device 1 onto the skin and actuates the triggering element 5.

The functioning of the injection device 1 is explained with reference to the schematic illustrations in FIGS. 2 to 6. The structural configuration shown is used merely for the simple explanation. FIG. 2 shows the injection device 1 in an unactuated state. The injection needle 7 has a cannula holder 23 to which a cannula 22 is fixed. The cannula 22 protrudes out of the housing 2 with a length (a) which corresponds to the insertion depth. During the injection operation, the housing 2 is placed by the proximal end side thereof, which forms a support 35, onto the skin.

In the housing 2, a container 10 is arranged in the region of the first housing part 3. The container 10 is advantageously designed as a carpule and, at the distal end thereof, has a stopper 26 which is moved in the proximal direction in order to expel injection fluid through the cannula 22 arranged at the proximal end of the container 10. The distal end of the stopper 26 has an end side 56 against which a plunger 17 bears with an end side 27. The plunger 17 serves for moving the stopper 26. In addition, the plunger 17 is part of a driving device which displaces the container 10 in the housing 2 in the direction of a longitudinal axis 30 of the injection device 1. For this purpose, the plunger 17 is designed as a rack and has teeth 18 on at least two sides which are arranged lying opposite each other in the exemplary embodiment. A pawl 16 which is mounted on a holder 11 engages in one of the rows of teeth of the plunger 17. The container 10 is arranged in the holder 11. The pawl 16 forms a coupling element 39 for connecting the holder 11 to the plunger 17. A pawl 20 which is mounted on a driving element 19 engages in the other row of teeth, which, in the schematic illustration, is arranged on the side opposite the pawl 16. The teeth 18 of the plunger 17 are designed in the form of saw teeth and have a flat profile on the proximal flank 68 thereof and a steep profile, in particular approximately perpendicular to the longitudinal axis 30, on the distal flank 69 thereof. On account of the dissimilar configuration of the proximal and distal flanks (68, 69) of the teeth 18, the holder 11 and the driving element 19 can be displaced in relation to the plunger 17 only in the distal direction. The movement in the opposite direction is blocked on account of the configuration of the teeth 18.

The driving element 19 is spring-mounted in relation to the housing 2 via a tension spring 21. The tension spring 21 is supported on a shoulder 33 of the driving element 19. A latching element 60, which can latch into a recess 29 of the housing 2, is arranged on the driving element 19. The driving element 19 together with the tension spring 21, the pawls 16 and 20 and the plunger 17 form a driving device which moves the container 10 relative to the housing 2 and the plunger 17 relative to the container 10.

In order to tension the injection device 1, the operator pulls the tensioning element 6 in the distal direction in the direction of the arrow 31, that is upward in FIG. 2. The entire tensioning distance (b) is the distance which the latching element 60 covers until it latches in the recess 29. If the tensioning element 6 is retracted from the inoperative position shown in FIG. 2, first of all the entire unit made of driving element 19, plunger 17, holder 11 and container 10 is displaced in the housing 2. In the process, the tension spring 21 is tensioned. When the tensioning element 6 is retracted in the direction of the arrow 31, the pawl 20 is arranged adjacent to a blocking contour 24 which prevents the pawl 20 from moving outward away from the plunger 17 and being able to release the latching connection between the pawl 20 and the plunger 17. The driving element 19 and the plunger 17 are fixedly connected to each other in this position via the pawl 20. A movement of the pawl 16 in the proximal direction in relation to the plunger 17 is blocked because of the geometry of the teeth 18. When the tensioning element 6 is retracted from the position shown in FIG. 2 into the position shown in FIG. 3, the pawl 16 arrives in the region of the blocking contour 28 (FIG. 3) which blocks a lateral movement of the pawl 16 and therefore release of the latching connection between the pawl 16 and the plunger 17. As a result of the blocking contours 24 and 28, driving element 19, plunger 17 and holder 11 are fixedly connected to one another.

As FIGS. 2 and 3 show, the holder 11 has an outwardly protruding projection 12 which is arranged in a recess 13 of the housing 2. In the position shown in FIG. 2, the projection 12 is arranged on a first, proximal stop 14. When the tensioning element 6 is retracted, the projection 12 moves to a second, distal stop 15. In the process, the holder 11 with the container 10, the plunger 17 and the driving element 19 cover a set distance (c) which corresponds to the distance by which the cannula 22 is pulled into the housing 2. FIG. 3 shows the injection device 1 after the cannula 22 is retracted into the housing 2. On further pulling of the tensioning element 6 out of the position shown in FIG. 3 in the direction of the arrow 31 in FIG. 2, a further movement of the holder 11 is blocked by the projection 12 which bears against the stop 15. The plunger 17 is fixedly connected to the holder 11 via the pawl 16, and therefore the plunger 17 cannot be moved further in the distal direction. In the position shown in FIG. 3, the pawl 20 is arranged in the region of a recess 25 on the housing 2 and can therefore slide radially outward and, when the tensioning element 6 is pulled further out in relation to the plunger 17, can move in the distal direction via a tooth 18. In the process, the tension spring 21 is tensioned further until the driving element 19 enters into the position shown in FIG. 4. As soon as the driving element 19 has moved relative to the plunger 17 by a tooth 18, the latching element 60 latches in the recess 29 of the housing 2 such that no further distal movement of the tensioning element 6 is possible.

FIG. 4 shows the injection device 1 in the completely tensioned position. In this position, the operator places the injection device 1 by the support 35 onto the skin and actuates the latching element 60 in the direction of the arrow 32. This advantageously takes place via the triggering element 5, which is not shown in FIGS. 2 to 6. As a result, the latching connection between latching element 60 and recess 29 is released. As a result of the energy stored in the tension spring 21, the driving element 19 is moved in the direction of the arrow 36 shown in FIG. 5. In the process, the driving element 19 carries along the plunger 17 via the pawl 20. The pawl 20 has moved from the recess 25 to the blocking contour 24 and cannot deviate in the radial direction. The pawl 16 is arranged in the region of the blocking contour 28 and likewise cannot deviate, and therefore the holder 11 and the container 10 and also the injection needle 7 are also moved in the proximal direction. A relative movement of driving element 19 and holder 11 in the distal direction in relation to the plunger 17 is also not possible because of the configuration of the distal flank 69 of the teeth 18.

Upon the movement of the holder 11, the cannula 22 emerges out of the housing 2 at the proximal end and is inserted into the operator's skin. During this movement of the holder 11 relative to the housing 2, the projection 12 moves in the recess 13 from the distal stop 15 to the proximal stop 14, specifically by the regulating distance (c). This position is shown in FIG. 5. As a result of the force stored in the tension spring 21, the driving element 19 is moved further in the proximal direction. After the insertion operation, the pawl 16 is arranged in the region of the recess 13 and can move outward in relation to the plunger 17 and latch against the next tooth 18. The holder 11 cannot move further because of the bearing of the projection 12 against the stop 14. During the proximal movement of the driving element 19 out of the position shown in FIG. 5 into the position shown in FIG. 6, the driving element carries along the plunger 17, which moves relative to the container 10 and displaces the stopper 26 in the container 10 and thereby expels injection fluid through the cannula 22. In the process, the plunger 17 covers a metering distance (d) which corresponds to the spacing of the distal end side of two consecutive teeth 18. The metering distance (d) and the regulating distance (c) together correspond to the tensioning distance (b), which is shown in FIG. 2. In the case of injection devices in which the quantity of fluid to be injected can be set, the metering distance (d) can be set by the operator.

FIG. 7 shows the structural configuration of the injection device 1. FIG. 7 shows the injection device 1 in a partially tensioned state, in which the container 10 is arranged in the distal end position thereof, but the driving element 19 has not yet been displaced in the distal direction in relation to the plunger 17. This corresponds to the position shown in FIG. 3. The tensioning element 6 is guided on a guide sleeve 43 which is connected fixedly to the second housing part 4. In addition, a sleeve 40 is fixedly connected to the second housing part 4. The sleeve 40 and the second housing part 4 could also be formed as a single part. As a result of the two-part configuration, the production is simplified. The sleeve 40 bears with a radially outwardly protruding edge 41 against a step 42 of the housing part 4. The tensioning element 6 is fixedly connected to the driving element 19 at a connection 44. A single-part configuration of the two elements can also be provided here. The plunger 17 is guided in the interior of the driving element 19. The pawl 20 is formed on the driving element 19. The driving element 19 is made of plastic and the pawl 20 is integrally formed on the driving element 19 and is configured as an arm projecting in the direction of the longitudinal axis 30. The pawl 20 is resilient because of the inherent elasticity of the material.

The pawl 16 which is integrally formed on a cylindrical section 59 of the coupling element 39 is arranged on the side opposite the pawl 20. The coupling element 39 is also made of plastic, and the pawl 16 is formed on an arm which is resilient because of the inherent elasticity of the material.

The proximal end of the sleeve 40 has latching fingers 46 on which the coupling element 39 is latched. The coupling element 39 here is movable in the proximal direction in relation to the sleeve 40. The coupling element 39 is connected fixedly to the holder 11. The plunger 17 bears against the stopper 26. As FIG. 7 shows, the proximal end of the holder 11 has a receptacle 8 for the injection needle 7; the receptacle is designed as an external thread onto which the injection needle 7 can be screwed by the cannula holder 23 thereof. In the retracted position of the holder 11 that is shown in FIG. 7, the proximal end side 37 of the receptacle 8 has a spacing (e) from the support 35.

FIG. 8 shows the arrangement from FIG. 7 with an injection needle 7 arranged on the receptacle 8. The proximal end of the injection needle 7 has a tip 55 which is arranged within the first housing part 3. Accordingly, the tip 55 does not protrude beyond the support 35. The tip 55 has a spacing (o) from the support 35. The spacing (o) here can be very small. As FIG. 8 also shows, the cannula 22 protrudes through a membrane 38 of the container 10 into the interior of the container 10.

FIG. 9 shows the injection device 1 in the inoperative state. In this state, the container 10 is arranged in the proximal end position thereof, and the cannula 22 of the injection needle 7 protrudes beyond the support 35. The injection device 1 is in this state after an injection, before the injection needle 7 has been removed, and before tensioning of the injection device 1 after a new injection needle 7 has been placed thereon. In this inoperative state, the cannula 22 protrudes beyond the support 35. The tip 55 of the cannula 22 has the spacing (a) from the support 35. The cannula holder 23 is completely arranged within the housing part 3 and has a spacing (m) from the support 35. This prevents the cannula holder 23 from being able to come into contact with the operator.

FIGS. 9 to 15 show the sequence during the production of the injection device 1. The installation of the driving device is not shown specifically here. The driving device has already been fitted and arranged in the second housing part 4. The sleeve 40 protrudes here beyond the proximal end side 34 of the second housing part 4. The latching fingers 46 on which the cylindrical section 59 of the coupling element 39 is latched are arranged at the proximal end of the sleeve 40. The cylindrical section 59 has a stop 45. Between the stop 45 and the proximal end 52 of the coupling element 39, the coupling element 39 has an edge 47 which has longitudinal webs 48 running parallel to the longitudinal axis 30. The longitudinal webs 48 are configured as elevations, and therefore pockets which can serve to receive adhesive are formed between the longitudinal webs 48.

During the installation, the container 10 is first of all arranged in the holder 11. The holder 11 is subsequently pushed in the direction of the arrow 53 onto the edge 47. Before the holder 11 is pushed thereon, adhesive is arranged on the edge 47, if the holder 11 is intended to be adhesively bonded to the coupling element 39. The container 10 protrudes into the interior of the edge 47, and the holder 11 engages over the edge 47. As FIG. 11 shows, an annular space 49 which is bounded in the longitudinal direction 30 by a shoulder 51 on the holder 11 is formed between the holder 11 and the container 10. The shoulder 51 and the stop 45 limit the maximum insertion depth. The holder 11 is pushed onto the edge 47 until the end side 56 of the stopper 26 bears against the end side 27 of the plunger 17. The position of the stopper 26 in the container 10 is subject to comparatively large tolerances. For example, the position of the stopper 26 can fluctuate by approximately one millimeter from container to container. The end side 56 has a spacing (n) from the end side 37 of the receptacle 8, the spacing varying according to the position of the stopper 26. As FIG. 11 shows, the proximal end of the holder 11 has a thread 50 which forms the receptacle 8. The thread 50 is configured in such a manner that the cannula holder 23 (FIG. 9) can be screwed on until onto the end side 37 of the holder 11. This defines the position of the tip 55 of the injection needle 7 in relation to the holder 11.

After the holder 11 has been screwed onto the coupling element 39, the holder 11 and the coupling element 39 are connected fixedly and nonreleasably to each other. This can take place, for example, via adhesive bonding. The holder 11 is advantageously transparent, and the adhesive bonding is undertaken with an adhesive which cures under radiation, in particular under UV radiation. A nonreleasable connection by means of pressing, in particular via hot pressing, or via welding, in particular via laser welding or via ultrasonic welding, can also be provided. FIGS. 12 and 13 show the position of the holder 11 after the positioning and fixing on the coupling element 39. The stop 45 has a spacing (f) from the holder 11. The coupling element 39 protrudes by an insertion depth (g) into the annular space 49. The coupling element 39 here has a spacing (h) from the shoulder 51. The dimensions of the annular space 49 and the position of the stop 45 are selected in such a manner that, in the case of all of the tolerances which occur, the spacing (f) is formed between holder 11 and stop 45 and the spacing (h) is formed between coupling element 39 and the shoulder 51. The proximal end side 37 of the holder 11 has a spacing (i) from the proximal end side 34 of the housing part 4, the spacing being dependent on the position of the stopper 26.

After the holder 11 is fixed, the second housing part 4 is positioned on the first housing part 3 and is fixed thereon. This is shown in FIGS. 14 and 15. The first housing part 3 is inserted from the proximal side in the direction of the arrow 54 into the second housing part 4. The second housing part 4 engages over the first housing part 3. The first housing part 3 is positioned on the second housing part 4 in such a manner that a defined spacing (1) is produced between the end side 37 of the holder 11 and the support 35. This spacing in the proximal position of the holder 11 and of the container 10 that is shown in FIG. 15 is selected in such a manner that a desired insertion depth is produced for an injection needle 7 arranged on the receptacle 8. In this position, the cannula holder 23 is advantageously arranged within the first housing part 3. The first housing part 3 is positioned by changing the spacing (k) between the support 35 and the proximal end side 34 of the second housing part 4. As soon as the desired spacing (l) is set, the first housing part 3 is fastened nonreleasably to the second housing part 4. The fastening is advantageously undertaken via adhesive bonding, pressing, in particular hot pressing, or welding, in particular laser welding or ultrasonic welding.

In the exemplary embodiment of an injection device 61 that is shown in FIG. 16, the end side 27 of the plunger 17 does not bear against the end side 56 of the stopper 26 but rather has a defined spacing (p) therefrom. In this exemplary embodiment, the pushing of the holder 11 onto the coupling element 39 does not take place until the plunger 17 bears against the stopper 26, but rather until the defined spacing (p) is achieved. In order to ensure that, during the first injection, the stopper 26 is moved by the desired metering distance (d), the first tooth 57 over which the pawl 20 slides has a height (q) which is greater than the metering distance (d), specifically is greater than the latter by the spacing (p). As a result, during the first injection operation, the plunger 17 is adjusted by the spacing (p) as far as the stopper 26 and is additionally adjusted by the metering distance (d). The first tooth 58 over which the pawl 20 slides is of correspondingly enlarged configuration, and therefore the plunger 17 bears against the stopper 26 after the first injection operation.

It is understood that the foregoing description is that of the preferred embodiments of the invention and that various changes and modifications may be made thereto without departing from the spirit and scope of the invention as defined in the appended claims.

What is claimed is:

1. A method for making an injection device including a housing having a first housing part and a second housing part, the first housing part being firmly mounted to the second housing part such that the first housing part is immovable relative to the second housing part, a support configured to be applied to skin of a patient prior to a triggering of an injection, the first housing part having a proximal end side which forms the support such that the support is immovable with respect to the first housing part, a receptacle configured for an injection needle and to move relative to the housing between a distal end position and a proximal end position, wherein, in the proximal end position, a proximal end of the receptacle is located distal to a proximal end of the support, and a driving unit connected to the receptacle and configured to move the receptacle relative to the second housing part between the distal end position and the proximal end position, the method comprising the method steps of:

attaching the receptacle to the second housing part such that the receptacle is movable from the distal end position to the proximal end position;

after said step of attaching the receptacle to the second housing part, positioning the first housing part on the second housing part such that the receptacle, when in the proximal end position thereof, has a predetermined position relative to and distal to the proximal end of the support; and, non-releasably fixing the first housing part relative to the second housing part after said step of positioning of the first housing part on the second housing part, wherein an injection depth of the injection device is based on the proximal end position of the receptacle.

2. The method of claim 1, wherein the injection device further includes a container with injection fluid, the container having a movable plug arranged therein, the driving unit having a plunger configured to act on the movable plug, the method further comprising steps of:

positioning the container relative to the plunger so as to cause the movable plug to have a defined position relative to the plunger; and, fixing the container in said defined position relative to the plunger.

3. The method of claim 2, wherein said step of positioning of the container relative to the plunger is performed before said step of positioning of the first housing part on the second housing part.

4. The method of claim 2, wherein the injection device has a pawl configured to interact with the plunger, the method further comprising a step of fixing the container relative to the pawl after said step of positioning of the container relative to the plunger.

5. The method of claim 4, wherein the injection device further includes a holder configured to carry the receptacle therein, the method further comprising the steps of:

arranging the container in the holder; and, fixing the holder with the container arranged therein to the pawl.

6. The method of claim 1, wherein said step of non-releasably fixing the first housing part relative to the second housing part is achieved via one of adhesive bonding, pressing, and welding.

7. An injection device comprising:

a housing having a first housing part and a second housing part;

said first housing part being non-releasably fixed to and immovable relative to said second housing part;

a support configured to be applied to skin of a patient before an injection is triggered;

said first housing part having a proximal end side which forms the support such that the support is immovable with respect to the first housing part;

a receptacle configured for an injection needle, wherein the receptacle is movably attached to the second housing part between a distal end position and a proximal end position;

a container having a movable plug arranged therein;

a holder wherein said container is arranged in;

said holder having said receptacle for said injection needle;

a driving unit connected to said receptacle and configured to move said receptacle relative to said second housing part between the distal end position and the proximal end position, said driving unit having a plunger configured to act on said movable plug, wherein said driving unit further comprises a pawl connected to said containers; and said pawl configured to interact with said plunger and further configured to fix said plunger relative to said container and to release said plunger relative to said container, in dependence on an operating state of said injection device;

wherein said holder is connected to said pawl via an adhesive bond; and, said first housing part having a position relative to said second housing part such that said receptacle, when in the proximal end position thereof, has a predetermined position relative to and distal to a proximal end of said support, wherein an injection depth of said injection device is based on the predetermined position of said receptacle.

8. The injection device of claim 7, wherein said first housing part and said second housing part are one of adhesively bonded, pressed, and welded to each other.

9. The injection device of claim 7, wherein said plunger is configured to rest against said movable plug prior to a first injection.

10. The injection device of claim 9, wherein:
said plunger has a distance (p) to said movable plug prior to the first injection;
said driving unit is configured such that said plunger travels over a first path during the first injection which is greater by said distance (p) than a second path required to expel a set amount of injection fluid.

11. The injection device of claim 7, wherein said adhesive bond is cured via radiation.

12. The injection device of claim 7 further comprising a tension spring configured to cause a movement of said container relative to said housing and a movement of said plunger relative to said container during an injection procedure.

13. The injection device of claim 7, wherein said pawl is a first pawl, and said injection device further comprising:
a second pawl;
said driving unit being connected to said container and to said plunger via said second pawl; and,
said second pawl being configured to be controlled in dependence upon the position of said driving unit and said plunger relative to said housing.

14. The injection device of claim 7, wherein said holder comprises an outwardly protruding projection arranged in a recess of said housing.

15. The injection device of claim 7, wherein said driving unit is mounted in relation to said housing via a spring.

16. The injection device of claim 14, wherein said recess is positioned on an interior surface of said second housing part.

17. The injection device of claim 14, wherein said recess comprises a proximal stop, and wherein said outwardly protruding projection of said holder abuts the proximal stop of said recess when said receptacle is in said proximal end position.

18. The injection device of claim 15, wherein said driving unit further comprises a latch configured to engage said housing when said spring is in a compressed state.

19. The injection device of claim 14, wherein said recess comprises a distal stop, and wherein said outwardly protruding projection of said holder abuts said distal stop of said recess when said receptacle is in said distal end position.

20. A method for making an injection device including a housing having a first housing part and a second housing part, the first housing part being mounted to the second housing part such that the first housing part is immovable relative to the second housing part, a support configured to be applied to skin of a patient prior to a triggering of an injection, the first housing part having a proximal end side which forms the support such that the support is immovable with respect to the first housing part, a receptacle configured for an injection needle and to move relative to the housing between a distal end position and a proximal end position, wherein, in the proximal end position, a proximal end of the receptacle is located distal to a proximal end of the support, a container with injection fluid, the container having a movable plug arranged therein, a holder having the container arranged therein, the holder configured to carry the receptacle, and a driving unit connected to the holder in which the receptacle is arranged, the driving unit being configured to move the receptacle and the holder relative to the second housing part, the driving unit being configured to move the receptacle between the distal end position and the proximal end position, the method comprising the method steps of:

attaching the holder to the second housing part such that the receptacle is movable from the distal end position to the proximal end position;

after said step of attaching the holder to the second housing part, positioning the first housing part on the second housing part such that the receptacle has a predetermined position relative to and distal to the proximal end of the support when the receptacle is positioned at the proximal end position so as to cause manufacturing tolerances to be compensated between individual parts of said injection device; and, non-releasably fixing the first housing part relative to the second housing part after said step of positioning of the first housing part on the second housing part, wherein an injection depth of the injection device is based on the proximal end position of the receptacle.

* * * * *

UNITED STATES PATENT AND TRADEMARK OFFICE
CERTIFICATE OF CORRECTION

PATENT NO.        : 10,272,210 B2                                    Page 1 of 1
APPLICATION NO.   : 14/153682
DATED             : April 30, 2019
INVENTOR(S)       : Joachim Keitel It is certified that error appears in the above-identified patent and that said Letters Patent is hereby corrected as shown below:

In the Claims

<u>In Column 11:</u>
Line 10: In Claim 7, delete "containers;" and insert -- container; -- therefor.

Signed and Sealed this
Nineteenth Day of November, 2019

Andrei Iancu
*Director of the United States Patent and Trademark Office*